(12) United States Patent
Tikkanen et al.

(10) Patent No.: US 7,406,855 B2
(45) Date of Patent: Aug. 5, 2008

(54) METHOD AND A SENSOR DEVICE FOR MEASURING PARTICLE EMISSIONS FROM THE EXHAUST GASES OF A COMBUSTION ENGINE

(75) Inventors: Juha Tikkanen, Tampere (FI); Mikko Moisio, Tampere (FI); Kauko Janka, Tampere (FI); Kimmo Pietarinen, Tampere (FI); Jorma Keskinen, Tampere (FI); Antti Rostedt, Tampere (FI)

(73) Assignee: Dekati Oy, Tampere (FI)

( * ) Notice: Subject to any disclaimer, the term of this patent is extended or adjusted under 35 U.S.C. 154(b) by 340 days.

(21) Appl. No.: 10/562,067

(22) PCT Filed: Jun. 22, 2004

(86) PCT No.: PCT/FI2004/050099

§ 371 (c)(1),
(2), (4) Date: Dec. 22, 2005

(87) PCT Pub. No.: WO2004/113904

PCT Pub. Date: Dec. 29, 2004

(65) Prior Publication Data

US 2006/0156791 A1    Jul. 20, 2006

(30) Foreign Application Priority Data

Jun. 24, 2003    (FI) .................................. 20030938

(51) Int. Cl.
*G01N 7/00*    (2006.01)
(52) U.S. Cl. ..................................... 73/23.31
(58) Field of Classification Search ................. 73/23.31
See application file for complete search history.

(56) References Cited

U.S. PATENT DOCUMENTS

| | | | |
|---|---|---|---|
| 2,950,387 A | 8/1960 | Brubaker | |
| 3,247,375 A | 4/1966 | Lovelock | |
| 3,742,475 A | 6/1973 | Liebermann et al. | |
| 4,456,883 A | 6/1984 | Bullis et al. | |
| 4,531,486 A | 7/1985 | Reif et al. | |
| 4,939,466 A | 7/1990 | Johnson et al. | |

(Continued)

FOREIGN PATENT DOCUMENTS

JP    60100046 A    6/1985

(Continued)

*Primary Examiner*—Hezron Williams
*Assistant Examiner*—Rodney Frank
(74) *Attorney, Agent, or Firm*—Venable LLP; Eric J. Franklin

(57) ABSTRACT

A method and a sensor device for determining particle emissions from exhaust gases of a combustion engine substantially during the use in an exhaust pipe system or a corresponding exhaust gas duct, in which method emitted particles contained in the exhaust gases are charged and the particle emissions are determined by measuring the electric charge carried by the emitted particles in the exhaust gas duct. The emitted particles are charged by varying the way of charging or the charging power with respect to time in such a manner that as a result of the charging, emitted particles brought into at least two different electrical charge states are present, wherein the charge of the emitted particles is further determined as a difference value/values measured from the emitted particles brought into said at least two different electrical charge states.

21 Claims, 7 Drawing Sheets

U.S. PATENT DOCUMENTS

| | | |
|---|---|---|
| 4,959,010 A | 9/1990 | Burtscher et al. |
| 5,260,249 A * | 11/1993 | Shiraishi et al. ............. 502/304 |
| 5,475,311 A | 12/1995 | Cho et al. |
| 2002/0000810 A1 | 1/2002 | Bauer et al. |
| 2003/0006778 A1 | 1/2003 | Aiki et al. |

FOREIGN PATENT DOCUMENTS

| | | |
|---|---|---|
| JP | 63255651 A | 10/1988 |

* cited by examiner

METHOD AND A SENSOR DEVICE FOR MEASURING PARTICLE EMISSIONS FROM THE EXHAUST GASES OF A COMBUSTION ENGINE

CROSS-REFERENCE TO RELATED APPLICATIONS

The present invention claims priority from Finnish patent application 20030938 filed Jun. 24, 2003 and is the U.S. National Phase under 35 U.S.C. §371 of PCT/FI2004/05099 filed Jun. 22, 2004.

Field of the Invention

The invention relates to a method for measuring particle emissions from the exhaust gases of a combustion engine. The invention also relates to a sensor device implementing the method.

BACKGROUND

Exhaust gas emissions from traffic, particularly road traffic, constitute a significant part of harmful emissions inflicted by human activity on the environment. In addition to the detrimental gaseous emissions, such as carbon monoxide (CO), hydrocarbons (HC) and nitrogen oxides ($NO_x$), the fine particles contained in exhaust gases from vehicles have been found to be a significant health hazard, and therefore, certain upper limits for fine particle emissions have also been set by legislation. The trend is to continuously and gradually reduce said limit values and simultaneously to bring them to a uniform international level. Authorities setting the limit values for exhaust gas emissions include, for example, the European Commission and the United States Environmental Protection Agency (US-EPA).

Simultaneously with the development of combustion engine technology with the aim of always reducing the exhaust gas emissions, the control and diagnostic systems of the engines become more and more significant. A common concept in the field is so-called OBD (On-Board Diagnostics) sensors, which refer to sensors controlling the control systems of a vehicle and/or monitoring the function of certain components in the vehicle.

OBD sensors will also be increasingly used to control that particle emissions from the exhaust gases of vehicles remain within allowed limit values. A particular application in view of this invention is the checking, indication and/or control of the function of so-called particulate traps used in the exhaust gas systems of vehicles. These particulate traps are used especially in the exhaust gas systems of Diesel vehicles. Having collected particles for a given time, such a particulate trap requires so-called regeneration, in which regeneration the particles contained in the particulate trap are typically burnt by methods known as such, for example by increasing the temperature of the particulate trap and by simultaneously introducing into the particulate trap a sufficient quantity of air required for burning the soot particles.

U.S. Pat. No. 4,939,466 presents a measuring method and a device for indicating the operation of renegenerating the particulate trap of a Diesel vehicle. The arrangement is based on the use of an electrical charge sensor placed after the particulate trap in the exhaust duct. The particles developed during the regeneration have a natural electrical, typically positive charge which can be detected by a sensitive charge sensor placed in the exhaust duct. According to the teachings of said reference, the charge sensor can be an inductive annular electrode, or it may also have a net-like structure. The sensor is capable of detecting when the regeneration of the particulate trap occurs.

U.S. Pat. No. 4,456,883 presents a method and a device for determining the operation of a combustion engine by measuring particle emissions from the exhaust gases. The measuring arrangement comprises an electrostatic sensor placed in the exhaust duct to detect the periodic particle emissions from the different cylinders of the engine on the basis of the natural charge obtained by the particles in connection with the combustion. The cyclic measurement result can be averaged to determine the average particle emission, or the measurement result can be analyzed with respect to time to detect problems occurring in the operation of a single cylinder.

In the above-mentioned techniques for detecting particles under exhaust duct conditions by utilizing the natural charging of the particles, problems are caused by the fact that the natural charging of the particles is dependent on a large number of different factors, such as the quality of the fuel as well as, in a very complex way, the operating conditions and the loading of the engine. Furthermore, when a particulate trap or filter is used before the measuring point, the measurement result is also affected by the fact that the particulate trap or filter, as such, affects the electric charge of the particles passed through in a very complex way.

Solutions are also known from prior art which do not rely solely on the natural charging of particles contained in the exhaust gas but which use a separate charger for charging the particles before the measuring point.

JP 63255651 discloses a particle measuring sensor in which particles contained in exhaust gas are charged by a cathode electrode, and when they further impinge on an anode electrode, their electrical charge is detected on the basis of a sensitive current measurement.

JP 60100046 discloses a particle measuring sensor placed in an exhaust duct and comprising charging electrodes placed before measuring electrodes in the flow direction of the exhaust gas. By the high-voltage charging electrodes, particles contained in the exhaust gas are negatively charged before they are detected by the measuring electrodes.

However, when a separate charger is used according to the prior art for charging the particles, the following problems will be caused in practice.

In principle, the exact measurement of the number of the particles will require that also the charge of the particles must be known exactly. In the solutions of prior art, the measurement result will be affected by the natural charge obtained by the particles in connection with the combustion, because said charge is added to the charge obtained by the particles in the charger. This will cause a significant inaccuracy in the measurement result. The effect of the original, natural charge of the particles can be reduced by using sufficiently long retention times as well as a sufficiently high charge density for the particles in the charger, wherein all the particles are charged substantially in the same way, achieving a balanced charge. In practice, however, the result is that impractical large-size and powerful chargers must be used in vehicles. Furthermore, such powerful chargers act, as such, partly in the manner of an electrical filter and tend to remove some of the particles to be measured from the range of the charger. Thus the particles accumulated in the charger induce both a measuring error and the soiling of the charger.

In all cases, for measuring particle emissions on the basis of the electrical charge of the particles after a particulate trap or filter placed in the exhaust duct, one must measure relatively small currents, typically in the order of picoamperes, due to the relatively small number of the particles. This is difficult to implement under the demanding conditions of the exhaust duct, particularly for the following reasons. First of all, the temperature of the exhaust gases is high, typically several hundreds of degrees centrigrade at the measuring point, which causes significant leakage currents in the insulators of the electrodes placed in the exhaust duct and, further, significant current noise and drift of bias currents due to the elevated temperature of the components at the measuring amplifier placed in the vicinity of the electrode. Secondly, the exhaust gases contain impurities which soil the insulators. In the long run, the soiling of the insulators will increase leakage currents and noise in the current signal to be measured, thereby causing an increasing error in the measurement results. A quite significant problem in the measuring devices placed in the exhaust duct is the soiling induced by soot particles which may involve both actual clogging of the sensor structure and impairing of the insulation capacity of all the electrical insulators connected to the sensor. Moreover, the soot deposits interfere with the operation of the ionization or charger electrodes.

BRIEF DESCRIPTION AND MOST SIGNIFICANT ADVANTAGES OF THE INVENTION

It is an aim of the present invention to solve the above-described problems which are typical of the methods and devices of prior art, by implementing a particle measurement based on the use of a separate charger in a novel and inventive way.

In the invention, a charger is used for charging particles, because in this way, the effect of a particulate trap or filter placed in the exhaust pipe system on the charge distribution of the particles which have passed it can be eliminated in a way known as such by charging the particles artificially first after said particulate trap or filter. However, the present invention is also capable of simultaneously solving the following problems of prior art.

The invention eliminates the need to use a powerful and thereby bulky and significantly electric power consuming charger for the purpose of preventing the original, natural charge of the particles from distorting the measurement result. At the same time, all the problems caused by the bulky and powerful charger are eliminated, including the tendency of the high-power charger to collect particles like an electrical filter and thus to be soiled, as well as to involve the soiling of insulators and/or the actual clogging of the sensor. As the tendency of soiling is reduced, the leakage currents from the insulators and the electrode structures are also reduced, which improves the accuracy and sensitivity of the measurement of small currents.

Thanks to the invention, the above-mentioned problems are solved at the same time by implementing the charging of the emitted particles contained in the exhaust gas in a limited volume in the charger and by varying the mode of the charger, i.e. its charging power or way of charging, with respect to time in a cyclic or pulse-like manner. Now, by using a charge measuring means, the charge of the particles is measured as a difference value from the charges generated to the particles by the charger in at least two different modes. Typically, these two different modes and the charge states of the particles obtained by them are such in which the charging power of the charger is switched on/off or its way of the charging is switched between negative charging and positive charging.

To attain these purposes, the present invention provides a method and a sensor device.

By means of the invention, the electrical power required of the charger can be kept low, because of e.g. the fact that the charging takes place in a limited volume, but the measuring accuracy still remains good in spite of the possible original, natural charge of the particles, because the measurement is now based on determining the difference value between two different modes. The original charge state of the particles does not have a substantial effect even in the case that the charging times of the particles in the charger are so short that the charge remains substantially below the balanced charge. Thanks to this feature, it is also possible to implement the charger in a compact physical size and simultaneously to avoid unnecessary soiling of the insulators and clogging of the sensor structures. At the same time, the "filtering effect" of the charger itself, that is, removing particles from the gas flow, and the error caused by it in the measurement result can also be eliminated.

Furthermore, in the use of the measuring method according to the invention, the leakage currents from the insulators do not affect the final result, because their effect is automatically compensated for in the difference measurement. Similarly, any drift of the measuring electronics affecting the small currents to be measured, as well as low-frequency noise from the measuring electronics, are automatically compensated for.

The invention thus makes it possible to implement a sensor to measure the particle content of exhaus gases which is particularly well suited for OBD use, the sensor also having a sufficient sensitivity for measurements to be taken after a particulate trap or filter.

Because the inventive and novel idea is, in this case, related particularly to the cooperation between the charger and the charge measuring means used for detecting the particles charged by the charger, and a difference measurement to be taken between two different charge states, both the charger and the charge measuring means can be implemented in a variety of ways which may also be known as such.

BRIEF DESCRIPTION OF THE DRAWING

The invention and its advantages will be more evident for a person skilled in the art from the appended more detailed description, in which the invention is explained by means of selected examples and with reference to the appended figures, in which.

DETAILED DESCRIPTION OF THE INVENTION

In the following, the invention will be described by using selected examples. However, it will be obvious that the invention is not limited solely to the embodiments specifically presented therein, but it is also possible to implement other embodiments by combining the principles shown in the examples in the scope of the claims to be presented hereinbelow.

Separate Charger Placed Before the Charge Measuring Means in the Exhaust Duct

Figure 1:
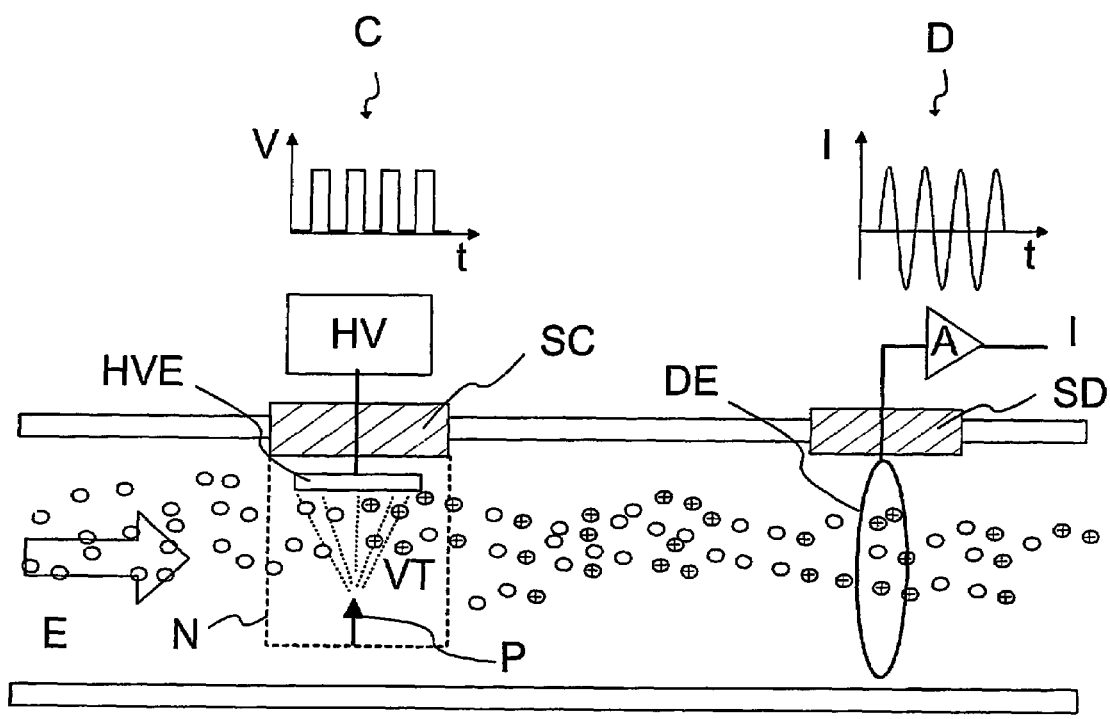
FIG. 1 shows, in a principle view, a first embodiment of the invention, based on the use of a separate charger and a charge measuring means.

In a first embodiment of the invention, a charger C is placed in an exhaust gas duct E as a separate component before a charge measuring means D in the direction of the current, as shown in principle in FIG. 1. FIG. 1 shows how the mode of the charger C, in this example case a corona charger, is changed in time by pulsing the voltage V generated by a high-voltage source HV. In addition to the high-voltage source HV, the charger C comprises an electrode HVE and a corona tip P which are placed in the exhaust gas duct E and between which an electric field is generated to charge the particles. The high-voltage supply of the electrode HVE through the wall of the exhaust gas duct E is led through an insulator SC. A limited volume VT, in which the particles are charged, is produced according to the invention by means of an electrode N with a preferably net-like design. In the charger C, the particles receive an auxiliary charge in addition to the natural charge which they have already before the charger.

The net-like electrode N defines the limited volume VT in which the particles are charged, by preventing free ions developed in the charger C from escaping from the volume defined by the electrode N. Without the electrode N, these ions, which have not transferred their charge to the particles contained in the exhaust gas, would be carried along with the exhaust gas to the charge measuring means D and be added in the measurement result. Within the limited volume VT defined by the electrode N, the electric field is arranged to be such that the field prevents the free ions from finding their way to and through the net-like electrode N. However, said electric field has no significant effect on the movements of charged particles, wherein the electrode only restricts the discharge of free ions from the charger C.

In FIG. 1, the charge measuring means D is arranged to measure the current I induced in the ring-shaped measuring electrode DE as the charged particles are carried along by the exhaust gas through said ring. The current detected by the measuring electrode DE is led through the insulator SD to an amplifier A. A similar charge measuring means is known from, for example, U.S. Pat. No. 4,456,883. The measuring electrode DE placed in the exhaust duct can also be rod-like or net-like, as is known from e.g. U.S. Pat. No. 4,939,466. Also other electrode structures for detecting charged particles, known as such and obvious for a person skilled in the art, are feasible. FIG. 1 also shows how the current I detected by the charge measuring means D varies in time as a result of changes in the mode of the charger C.

The essential feature in the invention is particularly the cooperation of the charger C and the charge measuring means D utilizing the fact that the particles are charged in a way varying in time; therefore, both the charger C and the charge measuring means D can be implemented in a variety of ways which may also be known as such.

More generally, the charging of the particles is based on the ionization of the gas carrying the particles, in this case the exhaust gas, and the migration of the ions thus produced onto the surface of the particles to be charged. This migration of the charges onto the surface of the particles is primarily based on the diffusion of the particles (so-called Brown diffusion) and/or an electric force generated by an external electric field. The gas carrying the particles can be charged in a number of different ways, for example by ionizing the gas with a radioactive (or other ionizing) radiation, by ionizing the gas with an electric discharge (e.g. corona discharge shown in FIG. 1), by heating a surface interacting with the gas to a temperature at which the surface emits electrons or charged particles (so-called thermal emission), by a strong electric field generated onto a conductive surface interacting with the gas (so-called field emission), or by energetic light focused on a surface interacting with the gas (so-called photoemission). Yet another method, known as such, is so-called direct photoionization which is based on an electron emission caused by electromagnetic radiation, for example light, in the substance.

In connection with the present invention, it is possible to use any of the above-mentioned particle charging methods or other methods obvious for a person skilled in the art, in the charger C. However, the corona charger, based on an electric discharge and shown in FIG. 1, is particularly suitable for the purpose, because it can be used to produce relatively high ion densities in the exhaust gas and in the limited volume VT in a stable way with reasonable electric currents and voltages. One essential advantage of the use of the corona charger is its property as such to prevent the accumulation of impurities in the electrode point P generating the charge. This feature is based on both electric forces and the protective gas flow (so-called corona wind) developing around the corona tip P.

Surprisingly, the inventors have also found that under the oxidizing conditions of exhaust gases from a Diesel engine, the corona discharge also has a directly cleaning effect on the corona head P in addition to the fact that the corona discharge slows down the accumulation of impurities on said electrode. This makes it possible to keep the corona tip P clean also in long-term use, which is essentially important in view of OBD applications. Obviously, this phenomenon is based on the effect of the oxidizing radicals produced by the electric discharge to burn off accumulating soot in the oxidizing gaseous atmosphere.

In the arrangement according to the invention, in which the charge is produced in cycles by switching the charging power of the charger C on and off, the corona tip P may still be soiled during the cycles in which the discharge is not on. If necessary, this problem is solved in an advantageous embodiment of the invention by implementing the switching between a positive and a negative corona current instead of alternating the charging event by switching the corona current on and off. Thus, the corona current that prevents the soiling of the corona tip P is always turned on, and only the direction of the current varies in cycles.

In the arrangement of the invention, the charge measuring means D used for detecting charged particles can also be implemented in several ways different from what is presented in FIG. 1 and in the following examples. If necessary, there may also be several charge measuring means D, wherein the measurements corresponding to the different modes (charging power or way of charging) of the charger C are taken with different charge measuring means, and the difference value between at least two different charge states according to the invention is determined, for example, from signals given by two different charge measuring means. In the invention, it is also possible to use more than two different charge states, wherein it is also possible to calculate several difference values. In this way, it is possible to improve the accuracy of the measurement result, such as linearity, in certain situations.

Charge Measuring Means Implemented in Connection with the Charger

Figure 2:
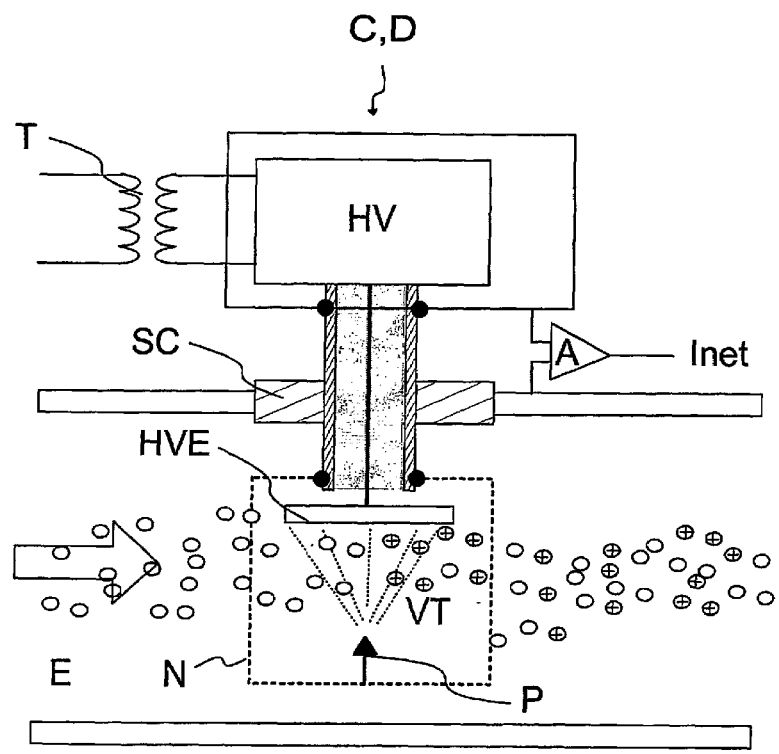
FIG. 2 shows, in a principle view, another embodiment of the invention, in which the charge measuring means is implemented in connection with the charger.

In another embodiment of the invention, the charger C and the charge measuring means D are integrated in a single compact structure as shown in principle in FIG. 2.

In the embodiment of FIG. 2, the total charge obtained by the particles in the charger C can be measured by measuring the net current discharged from the charger C. To measure this low (in the order of picoamperes) discharged net current, the charger C must be separated galvanically from the rest of the system, and the current measurement must be arranged between the galvanically separated charger C and a part in a galvanic connection with the exhaust gas duct E (the wall of the same).

In FIG. 2, the charger C is galvanically separated from the rest of the system by means of an isolation transformer T and an insulator SC. The measurement of the discharged net current Inet is arranged by an amplifier A to one electric pole of the charger C (the other pole is coupled to the electrode HVE). The amplifier A now measures the current discharged along with the charged particles from the charger C.

Instead of a corona charger, in the embodiment of FIG. 2 it is also possible to use a so-called spark charger, in which the gas sample containing particles in the sample volume VT defined by the net-like electrode N is charged by impinging it with quick electric discharges or electric breakdowns at intervals by high-voltage pulses. Even though these electric discharges produce both positive and negative ions in the gas, the result is—depending on the shape and size of the electrode arrangements—still a net charge with either sign. An advantage in the use of such a spark source is its effective self-cleanability and the insensitivity of the electric discharge phenomenon to the soiling of the structures and the electrodes as well as to deformations due to the wearing of the electrodes.

The above-presented pulse-like ion production and the charging of the particles on the basis of that is naturally very suitable for comparing two charge states by using an alternating current (AC) coupled measuring method, wherein it is possible to avoid the difficulties involved in measuring a direct current signal.

Implementation of the Charger on the Basis of Thermal Emission

Figure 3:
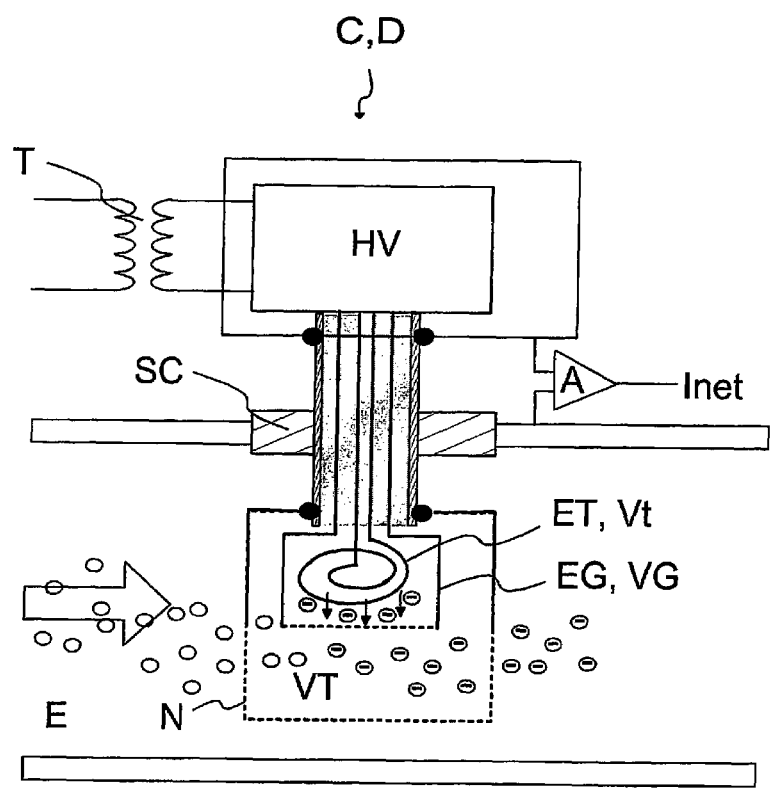
FIG. 3 shows, in a principle block chart, a third embodiment of the invention, based on the use of a thermal charger and electrostatic shielding.

In a third embodiment of the invention, the operation of the charger and the ionization of the gas are based on the utilization of thermal emission. FIG. 3 shows, in a principle view, an arrangement suitable for this purpose, in which the charger C and the charge measuring means D are combined in a way slightly similar to that in the embodiment of FIG. 2.

In the embodiment of FIG. 3, the charger C comprises two other electrodes in addition to the net-like electrode N, namely a thermal ionization electrode ET and a shielding electrode EG, whose mutual potential difference or its polarity can be varied in cycles. The ionization electrode ET is arranged to be heated, for example by resistive heating, wherein its hot/incandescent surface is used as a means for ionizing the gas/particles.

When the potential Vt of the ionization electrode ET is greater than the potential Vg of the surrounding shielding electrode EG, the negative ions produced thermally by the ionization electrode ET can move into the range of the electrode N and thereby into the space detected by the current measurement implemented by means of the amplifier A. On the other hand, when the potential Vg of the electrode EG is greater than the potential Vt of the electrode ET, the entry of negative ions into the range of the electrode N and to be measured is prevented. In this way, using the AC measuring method, the cycling of the mode of the charger C in time can be implemented by cycling the internal electric fields of the sensor, depending on the voltage Vt and Vg.

Figure 4:
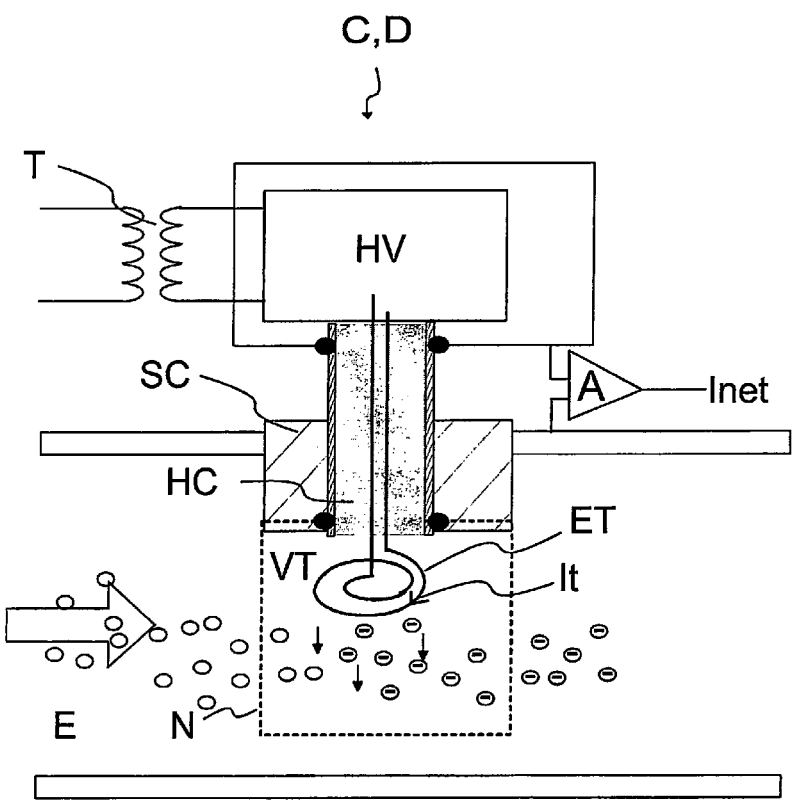
FIG. 4 shows, in a principle block chart, a fourth embodiment of the invention, based on the use of a thermal charger operating in cycles.

Another way to cycle the function of the thermal charger C is to pulse the heating of the surface that emits charged particles (electrons, ions), for example the ionization electrode ET. FIG. 4 shows, in a principle view, an arrangement in which the heating current It of the ionization electrode ET is varied in time to charge the particles in cycles. In this way, it is also possible to combine the production of ions needed for the charging and the cleaning of said surfaces from soot. It should also be noted that heat is also transferred by radiation from the heated (incandescent) ionization electrode ET to the insulator surfaces SC, HC in the vicinity, which makes it easier to keep them clean and thus reduces the leakage currents interfering with the measurement.

Other useful ion sources include a gas-ionizing radioactive source, such as a $Ni^{63}$ beta radiator or an $Am^{241}$ alpha radiator. The pulsing of the ion production can be achieved by an arrangement similar to that presented above for a thermal ion source in connection with FIG. 3 by coupling inner electric fields of the sensor. These electric fields can also be utilized in connection with other charging methods as, for example, in the use of a corona charger.

It will be obvious for a person skilled in the art that very high purity demands are set particularly for all those electric insulators which are surpassed by leakage currents which sum to the signal I, met to be measured. Under the conditions of the exhaust gas duct E, the increase in the temperature of the insulators also typically impairs their insulation capacity. Due to the low currents to be measured, it is necessary to place the measuring electronics in the immediate vicinity of the charge measuring electrode/electrodes, wherein the high temperatures in the exhaust gas duct of the vehicle also cause heating of the measuring electronics. This will increase e.g. noise caused by the measuring electronics.

The problems of impaired insulation capacity caused by the too high temperature of the electronics and the soiling and heating of the insulators are solved, in one embodiment of the invention, by combining the principles of air cooling of the electronics and the insulators as well as of protective air blowing to prevent soiling of the insulators.

Figure 5:
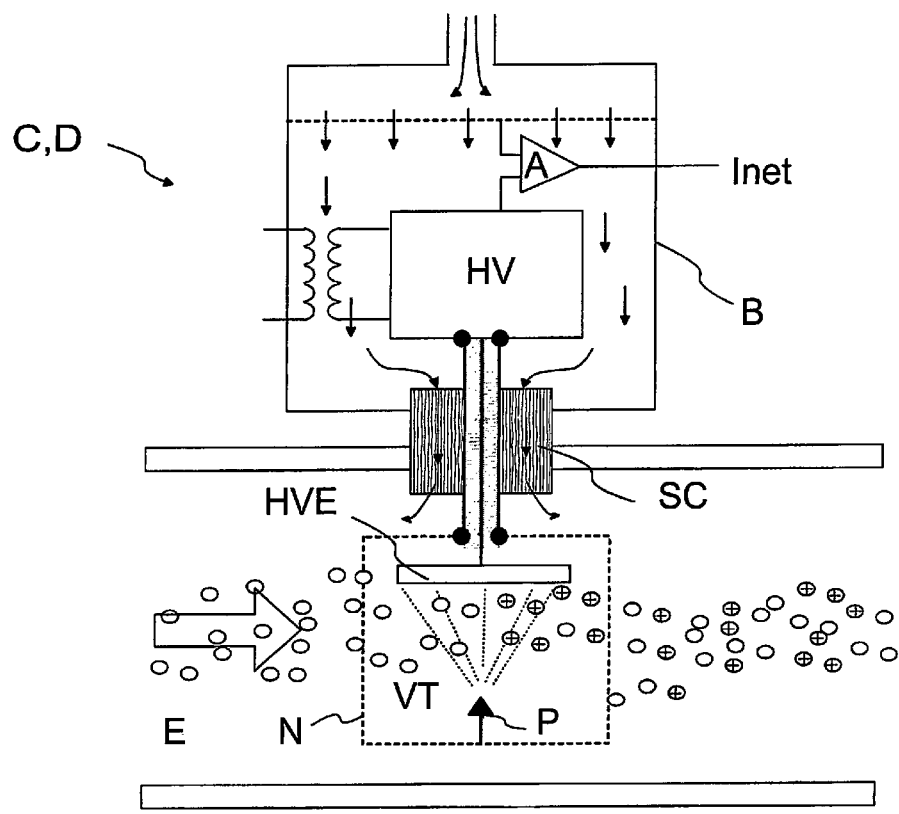
FIG. 5 shows, in a principle block chart, a fifth embodiment of the invention, based on the use of a gas flow for cooling and protecting from soiling.

FIG. 5 shows, in a principle view, an arrangement in which the insulator SC is made of a porous, gas-permeable material. The amplifier A and the high-voltage source HV including the measuring electronics are placed in a common housing B in such a way that when a gas (typically air) for cooling the measuring electronics is blown into the housing B, said gas is discharged completely or partly via the insulator SC into the exhaust gas duct E. The gas discharged through the insulator SC effectively prevents the surface of the insulator from being soiled at the same time when the gas cools both the insulator SC and the components inside the housing B.

As the charger of FIG. 5 is one based on the use of diffusion charging, i.e., for example a corona charger, it is possible to operate in such a range of ion content and charge volume that the charging of the particles is substantially dependent on the product of the ion density and the charging time only. In this situation, in the arrangement shown in principle in FIG. 5, the discharged charge (net current Inet) detected by the amplifier A is proportional to the particle content, irrespective of the rate of the gas flow passing through the charge volume defined by the net-like electrode N. In the comparative measurement to be taken for the difference measurement, it is possible to eliminate the effect of the original charge of the particles on the measurement result. This is realized particularly well when the cyclic coupling of the mode of the charger is made between the positive and the negative charge polarities.

In the following, we shall still discuss in more detail some facts to be taken into account in the implementation of sensor structures according to the invention.

The relative lengths in time of the charging cycles generated by the charger C (charger on/off cycles) may vary freely as required by each application. Said lengths in time may also be equal, wherein the charger operates at a pulse ratio of 1:1. The power of the charger in said charging cycles can also be selected to be other than 0 or 100%. If necessary, the charging power may also be varied in cycles between more than two different power levels. The frequency of the successive charging cycles may be selected according to the application in question, for example from 0.1 to 10 Hz.

Figure 6:
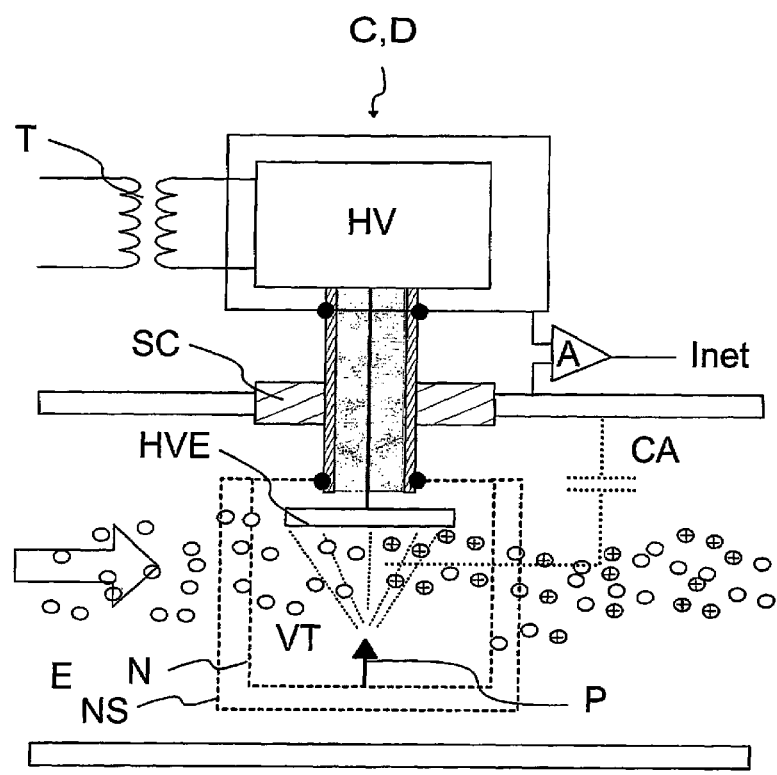
FIG. 6 shows, in a principle block chart, a way of implementing the electrostatic shielding.
Figure 7:
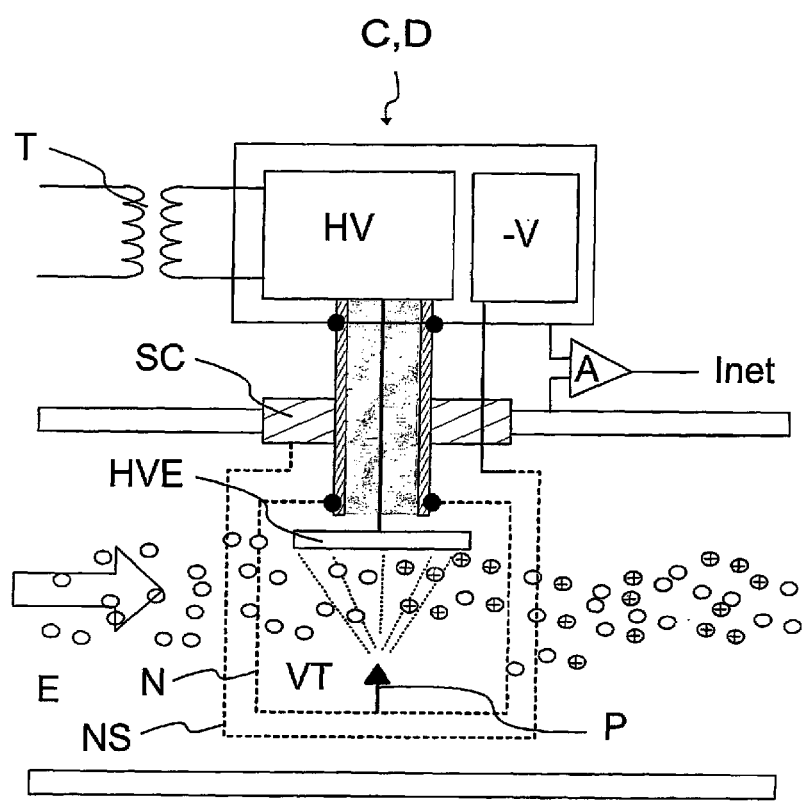
FIG. 7 shows, in a principle block chart, another way of implementing the electrostatic shielding.

FIGS. 6 and 7 show, in principle, solutions which further improve the electrostatic shielding of the sensor device according to the invention as well as reduce further the escape of ions from the sample volume VT.

One significant function of the net-like electrode N is to reduce stray capacitance which is developed between the electric field generated by the electrode HVE and the walls of the exhaust gas duct E. This stray capacitance, which is illustrated in FIG. 6 by a capacitor CA drawn by broken lines, affects the current Inet to be measured, causing a measurement error. Another function of the net-like electrode N is to use the electric field formed inside it to prevent the escape of free electrons from the sample volume VT, as already described above. To achieve these aims related to the electric function of the electrode N, the network or the like formed by the electrode N should be as dense as possible, wherein it is more difficult for the exhaust gas and the particles contained in it to flow through said electrode N, and the structure of the electrode may even be clogged completely.

In view of both the electronics and the flow technology, an optimal function is obtained by the arrangement of FIG. 6, in which the net-like electrode N defining a limited sample volume VT is enveloped by yet another net-like auxiliary electrode NS. Now, these electrodes N, NS together constitute an effective electrostatic shielding to prevent stray capacitance CA, and they also prevent efficiently the escape of free ions from the sample volume VT, even though the net-like or otherwise perforated structure of the electrodes were arranged to be loose/sparse by increasing the number/size of openings therein, wherein they are not clogged and do not prevent the flow of the exhaust gas and the particles through the sample volume VT. In view of the function in the sense of electric and flow technology, the combination of two or more successive sparse net-like electrodes N, NS provides a better compromise than merely one electrode.

As shown in FIG. 6, the outer auxiliary electrode NS can be electrically coupled to the electrode N or, as shown in FIG. 7, a potential −V different from the electrode N can be coupled to the auxiliary electrode.

It will be obvious for a person skilled in the art that in the sensor device according to the invention, the charge obtained in the sample volume VT by the single particles contained in the exhaust gas may be either the balanced charge or one below it. With a sufficient retention time of the particles, the particles obtain a balanced charge when passing through the sample volume, wherein the measurement result is primarily dependent on the product of the flow rate of the exhaust gas and the particle density. In a situation in which the retention time of the particles in the sample volume VT is shorter than that needed for producing the balanced charge, the measurement result is dependent on the product of the charge density of the sample volume VT and the retention time.

The invention claimed is:

1. A method for defining particle emissions from exhaust gases of a combustion engine in an exhaust pipe system or a corresponding exhaust gas duct substantially during the use, in which method emitted particles contained in the exhaust gas are charged and the particle emissions are determined by measuring the electric charge carried by the emitted particles in said exhaust gas duct, wherein the emitted particles are charged by varying the way of charging or the charging power with respect to time in such a manner that, as a result of said charging, emitted particles brought to at least two different electric charge states are present, wherein the charge of the emitted particles is further defined as a difference value/values measured from the emitted particles brought to said at least two different electric charge states.

2. The method according to claim 1, wherein the charging of the emitted particles is performed in a limited sample volume supplied with exhaust gas, to which ions and/or electrons are introduced by varying their content or polarity in time in a cyclic or pulse-like manner.

3. The method according to claim 2, wherein the charging power is varied in said sample volume substantially between on and off modes.

4. The method according to claim 2, wherein the way of charging is varied in said sample volume substantially between negative charging and positive charging.

5. The method according to claim 1, wherein the emitted particles are charged on the basis of electric corona discharge.

6. The method according to claim 1, wherein the electric charge obtained by the emitted particles is determined as the net charge obtained by them during the charging.

7. The method according to claim 6, wherein the emitted particles are charged galvanically by means of a charger separated from the rest of the system, and that the net charge obtained by the emitted particles is determined by measuring the discharging current carried along by them from said charger, which discharging current is measured between said charger and a point in a galvanic contact with the wall of the exhaust gas duct.

8. A sensor device for determining particle emissions from exhaust gases of a combustion engine in an exhaust pipe system or a corresponding exhaust gas duct substantially during the use, which device comprises at least one charger arranged in said exhaust gas duct for charging emitted particles contained in the exhaust gas, and at least one charge measuring means arranged in said exhaust gas duct for measuring the electric charge carried by the emitted particles, wherein said at least one charger is arranged to charge the emitted particles by varying the way of charging or the charging power with respect to time in such a manner that emitted particles brought to at least two different electric charge states are present, wherein said at least one charge measuring means is arranged to determine the charge of the emitted particles as a difference value/values measured from the emitted particles brought to said at least two different electric charge states.

9. The sensor device according to claim 8, wherein said sensor device comprises means for forming a limited sample volume, to which sample volume and to the exhaust gas introduced therein said at least one charger is arranged to produce ions and/or electrons by varying their content or polarity in cycles or in a pulse-like manner by varying the charging power or the way of charging of the charger.

10. The sensor device according to claim 9, said means for forming the limited sample volume consist of a single electrode having a net-like or other structure which is permeable to the flow of the exhaust gas and the emitted particles contained therein, or of several electrodes of the above-mentioned kind within each other.

11. The sensor device according to claim 8, wherein the charging power of said at least one charger is varied substantially between on and off states.

12. The sensor device according to claim 8, wherein the way of charging said at least one charger is varied substantially between negative charging and positive charging.

13. The sensor device according to claim 8, wherein said at least one charger is a charger based on thermal emission.

14. The sensor device according to claim 8, wherein said at least one charger is a charger based on the use of electromagnetic radiation.

15. The sensor device according to claim 8, wherein said at least one charger and said at least one charge measuring means are structurally integrated to form substantially one sensor structure.

16. The sensor device according to claim 8, wherein said at least one charger is arranged to be separate, before said at least one charge measuring means in the flow direction of the exhaust gas in the exhaust gas duct.

17. The sensor device according to claim 8, wherein said at least one charge measuring means is arranged to determine the electric charge obtained by the emitted particles as the net charge obtained by them from said at least one charger.

18. The sensor device according to claim 17, wherein said at least one charger is galvanically separated from the rest of the system and that said at least one charge measuring means is arranged to determine the net charge obtained by the emitted particles by measuring the discharging current carried along by them from said charger, which discharging current is measured between said charger and a point in a galvanic contact with the wall of the exhaust gas duct.

19. The sensor device according to claim 8, wherein the sensor device also comprises means for cooling said at least one charger and/or said at least one charge measuring means and components related thereto, by means of a gas flow.

20. The sensor device according to claim 19, wherein said gas flow is led through the structures of the sensor device and further into the exhaust gas duct through one or more porous and/or perforated components used as an electrical insulator, to cool said component and to prevent its soiling.

21. The sensor device according to claim 8, wherein the sensor device comprises means for eliminating noise currents caused by internal changes in the electric fields in the sensor device, on the basis of electrostatic shielding.

* * * * *